United States Patent [19]

Dorai et al.

[11] Patent Number: 5,434,315
[45] Date of Patent: Jul. 18, 1995

[54] REDUCING MOLECULAR WEIGHT POLYDISPERSITY OF POLYETHER GLYCOLS BY MEMBRANE FRACTIONATION

[75] Inventors: Suriyanarayanan Dorai, Hockessin, Del.; William W. Goudie, Kennett Square, Pa.; Sarah E. Ochsenhirt, Cincinnati, Ohio; Dhiren V. Patel, Middletown; James R. Cavall, Newark, both of Del.

[73] Assignee: E. I. du Pont de Nemours and Company, Wilmington, Del.

[21] Appl. No.: 199,399

[22] Filed: Feb. 22, 1994

[51] Int. Cl.$^6$ .................. C07C 43/11; C07C 43/18
[52] U.S. Cl. ................................ 568/621; 568/617
[58] Field of Search ........................ 568/621, 617

[56] References Cited

U.S. PATENT DOCUMENTS

| | | | |
|---|---|---|---|
| 3,478,109 | 11/1969 | McConnell | 260/611 |
| 3,925,484 | 12/1975 | Baker | 260/615 |
| 4,115,408 | 9/1978 | Baker | 260/346 |
| 4,163,115 | 7/1979 | Heinsohn et al. | 560/240 |
| 4,510,333 | 4/1985 | Pruckmayr | 568/617 |
| 4,585,592 | 4/1986 | Mueller | 260/408 |
| 4,762,951 | 8/1988 | Mueller | 568/617 |
| 4,933,503 | 6/1990 | Mueller | 568/621 |
| 4,946,939 | 8/1990 | Murphy et al. | 568/621 |

Primary Examiner—Johann Richter
Attorney, Agent, or Firm—Robert B. Stevenson

[57] ABSTRACT

Polyether glycols, especially poly(tetramethylene ether) glycols, having a narrow molecular weight distribution (e.g., Mw/Mn=1.2 to 1.80), are made by a process which consists of separating the low molecular weight fraction in an ultrafiltration module. In these units, molten PTMEG is fed at temperatures in the range of 30° to 150° C. and pressures ranging between 25 and 1500 psi. The PTMEG retentate from the ultrafiltration unit is also characterized by water content <25 ppm and low to negligible concentration of oligomeric cyclic ethers.

5 Claims, 1 Drawing Sheet

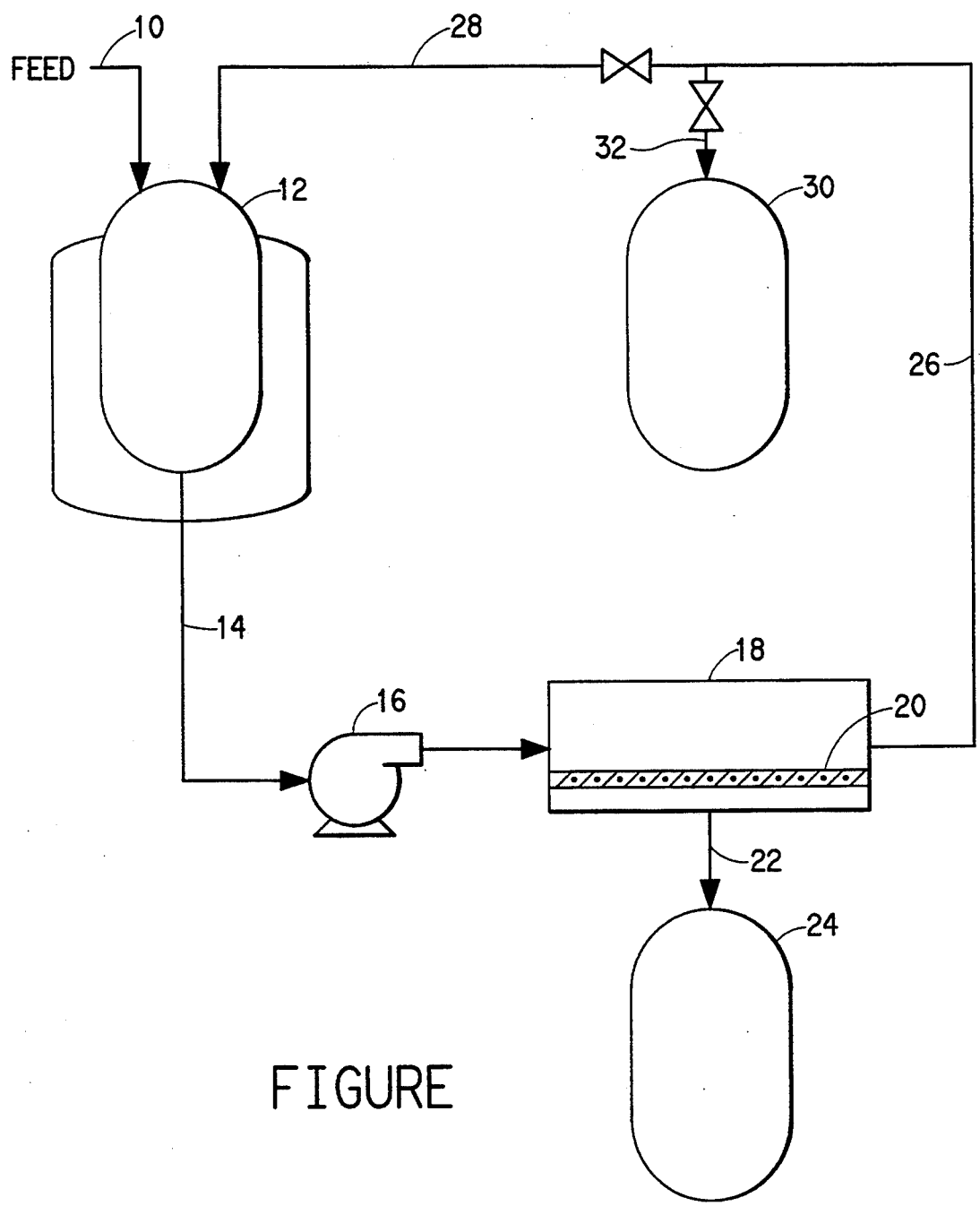
FIGURE

REDUCING MOLECULAR WEIGHT POLYDISPERSITY OF POLYETHER GLYCOLS BY MEMBRANE FRACTIONATION

BACKGROUND OF THE INVENTION

1. Field of the Invention

The present invention relates to a process for reducing the molecular weight polydispersity of polyether glycols, particularly poly(tetramethylene ether) glycols, by membrane fractionation. More specifically, the present invention involves an improved process for recovering PTMEG characterized as having a narrow molecular distribution and an unusually low polydispersity achieved by batchwise or continuous removal of low molecular weight species using a cross-flow ultrafiltration or membrane separation technique.

2. Description of the Related Art

It has long been recognized that a narrow molecular weight distribution and/or a numerically low polydispersity (i.e., $M_w/M_n$ where $M_w$ is weight average molecular weight and $M_n$ is the number average molecular weight) for poly(tetramethylene ether) glycols, PTMEG, is desirable for a number of end use applications in specialty polyurethanes and polyether esters based on the PTMEG building blocks; $-O+CH_2CH_2CH_2CH_2O)_{\overline{n}}$. Consequently, various methods of altering or controlling the molecular weight distribution of PTMEG have previously been suggested with varying degrees of commercial success.

For example, Japanese Kokai No. 85/42421 discloses treating broad molecular weight distribution PTMEG with a mixture of water and a solvent having poor dissolving power for PTMEG while U.S. Pat. No. 3,358,042 employs water, steam distilling and a water-immiscible polymer solvent and U.S. Pat. No. 3,478,109 suggests methanol extraction after dissolving the polymer in an organic solvent. U.S. Pat. Nos. 4,762,951 and 4,933,503 disclose a three phase separation technique preceded in the later patent by a low pressure distillation step to achieve a narrower molecular weight distribution product. U.S. Pat. No. 3,925,484 teaches a method of narrowing the molecular weight distribution by partial depolymerization in the presence of an acidic ion exchange resin and U.S. Pat. No. 4,585,592 suggests treating with an oxygen-containing gas with each being followed by low pressure distillation. In U.S. Pat. Nos. 4,163,115 and 4,510,333 a method of using an acylium ion precursor to polymerize THF is disclosed with the latter maximizing the tertiary oxonium ions prior to the polymer propagation thus leading to a narrow molecular weight distribution.

SUMMARY OF THE INVENTION

The present invention is viewed as an improved method for narrowing the molecular weight distribution of poly(tetramethylene ether) glycols by physical separation/fractionation of a polydisperse polymer melt. For example, the improved process is employed to prepare PTMEG having a molecular weight between about 400 and about 4,000 with a polydispersity between about 1.20 and 1.8 starting from a PTMEG having a correspondingly similar average molecular weight but a broader (i.e., numerically greater) polydispersity.

Thus, the present invention provides a process for fractionating poly(tetramethylene ether) glycols comprising the steps of:

(a) providing a cross-flow membrane fractionation means characterized by a permeable or semipermeable membrane surface having a feed/retentate side and a permeate/ultrafiltrate side for separating relatively lower molecular weight poly(tetramethylene ether) glycol species from relatively higher molecular weight poly(tetramethylene ether) glycol species;

(b) passing a feed stream of molten poly(tetramethylene ether) glycols, consisting of a distribution of poly(tetramethylene ether) glycol species substantially free of solvent, across the feed/retentate side of the membrane surface of the membrane fractionation means at a temperature above the melt temperature of the poly(tetramethylene ether) glycol and below the decomposition or melt temperatures of the membrane surface and poly(tetramethylene ether) glycol such that at least a portion of relatively lower molecular weight poly(tetramethylene ether) glycol species pass preferentially through the permeable or semipermeable membrane surface; and (c) recovering from the membrane fractionation means a permeate/ultrafiltrate fraction rich in lower molecular weight poly(tetramethylene ether) glycol species characterized by a numerically smaller polydispersity than the original feed stream of molten poly(tetramethylene ether) glycols and a retentate fraction rich in higher molecular weight poly(tetramethylene ether) glycol species also characterized by a numerically smaller polydispersity than the original feed stream of molten poly(tetramethylene ether) glycols.

BRIEF DESCRIPTION OF THE DRAWING

The FIGURE represents a simplified process-flow diagram according to one embodiment of the invention schematically illustrating the major components of the process and their interconnection.

DESCRIPTION OF THE PREFERRED EMBODIMENTS

The actual separation of relatively low molecular weight PTMEG species from relatively high molecular weight PTMEG species according to the present invention is achieved by what can be categorically viewed as an ultrafiltration process or a membrane separation process. In either case or perspective, the molten PTMEG being fractionated flows over the permeable or semipermeable surface (i.e., the membrane) thus sweeping across the surface and maintaining the desired flux rate through the membrane. Thus for purposes of this invention the term "membrane fractionation" is used to refer to ultrafiltration and membrane separation collectively while the additional term "cross-flow" is used to emphasize the sweeping of the surface by the molten polyether glycol being fractionated.

Since the PTMEG melt being fractionated is a continuous distribution of a series of oligomers and/or polymers essentially free of solvent (i.e., provided one does not arbitrarily view the lowest molecular weight oligomers as the solvent and the highest as the solute), the instant process can, at least in principle, be readily distinguished from reverse osmosis. More specifically, the instant process does not require the very high pressures associated with reverse osmosis (e.g., as high as 1200 psig) to drive pure solvent from a solution through a membrane impervious to the solute of that solution. Yet a more modest pressure gradient from the retentate side to the permeate/ultrafiltrate side analogous to many reverse osmosis applications is advantageously employed. The methodology employed in the instant invention can also be conceptually distinguished from most of the typical ultrafiltration or membrane separation processes in that the solventless melt being fractionated involves relatively viscous materials with no clear demarcation between which individual species are permeable and which are not. In other words the actual passing through the membrane or filter is perhaps more accurately viewed as a statistical event of decreasing probability with increasing molecular weight thus leading to both a permeate/ultrafiltrate fraction and a retentate fraction that compositionally are also distributions of oligomers/polymers; albeit, of narrower molecular weight distribution than the original feed composition.

The overall process for reducing the molecular weight polydispersity of polyether glycols according to the present invention, how it differs from yet is related to previously known separation techniques, what advantages there are associated with its use and under what circumstances the present invention provides these advantages can perhaps be best explained and understood by reference to the drawing. Thus the schematic flow diagram of the FIGURE is presented here to illustrate the basic components and stages of one particular embodiment of the present invention. As illustrated in this FIGURE, a feed stream consisting of a molten polyether glycol (e.g., PTMEG) characterized by a molecular weight distribution too broad-for a desired specific end use (as explained and exemplified later) is periodically introduced via line 10 to a heated and/or thermally insulated work tank 12. During separation of the lower molecular weight species or fraction from the starting feed material, the molten viscous polyether glycol is withdrawn from tank 12 via line 14 by circulating pump 16 and introduced into the cross-flow ultrafiltration/membrane unit 18. As the feed material sweeps across the membrane surface 20 the relatively lower molecular oligomers selectively and preferentially pass through the membrane to the permeate/ultrafiltrate side of the separation unit 18. The permeate/ultrafiltrate fraction characterized by a lower molecular weight and numerically smaller polydispersity than the original feed composition is withdrawn from the separation unit 18 via line 22 and sent to permeate product storage tank 24. The retentate exiting the separation unit 18 via line 26 is either returned to the working tank 12 via valved line 28 or sent to the retentate product storage tank 30 via valved line 32. Typically multiple passes through the separation unit 18 are required to remove a sufficient amount of low molecular weight species to elevate the retentate average molecular weight as well as narrow its molecular weight distribution, again relative to the starting composition, that it represents a commercially acceptable product or can be acceptably blended with commercial grade of product (as explained and illustrated more fully later). Consequently, during the separation or fractionation stage of the overall process the molten polyether glycol feed is continuously circulated in a closed loop fashion via valved line 28 with valved line 32 closed. Having ultimately achieved the desired degree of fractionation the valved line 28 is closed and residual retentate is dumped to the retentate product storage tank 30. After delivery of the retentate to the storage tank 30 a new batch of molten polyether glycol can be introduced into the working tank 12 and the entire cyclic process can be reinitiated. Thus in the specific embodiment being illustrated here the process according to the present invention: is technically and intentionally being operated in a batch mode. However, it is contemplated that multiple systems properly sized and arranged in parallel can be employed to effectuate a continuous mode of Operation. Similarly for purposes of this invention it is contemplated that a properly sized ultrafiltration/membrane unit 18 or more probably plurality of units can be operated continuously even to the extent of eliminating the need for a working tank. It should be further appreciated that the specific embodiment illustrated in the drawing in any commercially practical application or version will involve additional equipment not illustrated or shown. For example but not by way of limitation various throttle vanes to control or regulate flow, transfer pumps to move or deliver the viscous melt, various sensors .for measuring temperature, pressure, flow and fluid levels or the like as well as automated and/or manual control systems and equipment, all as generally known in the art, may advantageously be present.

The ultrafiltration/membrane unit useful in the present invention can categorically be any such system and equipment as generally known in the art including by way of example, but not limited thereto, thin layer (flat sheet) semipermeable membrane, spiral wound membrane, hollow fiber membrane, microporous or semipermeable anisotropic ultrafilter or the like. Typically the microporous or semipermeable surface and material being employed, will be nominally characterized by virtue of specifying a "so-called" approximate cut off value (ACOF) expressed as a function of molecular weight or by specifying a permeability relative to an arbitrarily selected compound or solution. For purposes of fractionating commercial PTMEG according to the present process this ACOF should be (if not literally then at least in principle) below about 2,000 molecular weight PTMEG as will be explained and exemplified more fully latter. In the case of using a true .membrane separation system, the material of choice would preferably consist of a polymeric membrane constructed mainly from either polysulfone or cellulose acetate derivatives and the like. Again any conventional commercially used configurations such as flat sheet, spirals or hollow fibers can be used and have been in the laboratory system as exemplified herein. In the case of using an ultrafilter arrangement, a tubular membrane consisting of sintered stainless steel coated With varying substrates or combination of substrates such as titanium dioxide, zirconium oxide, and polyacrylic acid is preferred. Other variations in construction may include filament-wound or braided, glass-fiber, or resin-reinforced tubes with a cellulose acetate semipermeable membrane inserted or cast into the interior surface of the tubular support.

The overall process according to the present invention is typically operated at between about 35° C. and about 150° C. Preferably all equipment in contact with the molten PTMEG is insulated or heat jacketed such as to prevent gelation or solidification as well as to maintain appropriate melt viscosities. The lower temperature limit is in principle established by the melt temperature of the particular polyether glycol being fractionated while the upper limit is a function of either the decomposition or softening of the membrane material (i.e., the polysulfone or cellulose acetate) in the case of membrane separation or the thermal stability, of the PTMEG melt in the case ultrafiltration (i.e., the sintered stainless steal). Thus, lower operating temperatures are necessary when the membrane fractionation unit is constructed of or involves polysulfone or cellulose acetate. However for sintered tubular membranes coated with specific substrates, temperatures higher than 100° C. degree can be used. At these higher temperatures, a significant increase in the polymer circulation rate is achieved because of reduced polymer viscosity.

The operating pressure is typically somewhat elevated such as to maintain the desired cross-flow of the molten PTMEG sweeping over the permeable or semipermeable surface. Advantageously the pressure at the inlet of the membrane unit is from about 100 to about 400 psig with a pressure drop relative to the retentate outlet being considerably less than this range. However, it should be appreciated that other pressures and pressure drops are contemplated as equivalent for purposes of the present invention provided the desired cross-flow is achieved.

In order to evaluate the affect and advantages associated with the use of the present invention certain terms which are typical molecular weight distribution parameters are used herein. Thus for purposes of describing the present invention: the number average molecular weight, Mn, is defined as $Mn = \Sigma N_i M_i / \Sigma N_i = \Sigma n_i M_i$ where $N_i$ is the number of moles, $M_i$ is the molecular weight and $n_i$ is the mole fraction of the "i th" oligomeric/polymeric member of the distribution (i.e., the "i th" specie); the weight average molecular weight is defined as $Mw = \Sigma N_i M_i^2 / \Sigma N_i M_i = \Sigma w_i M_i$ where $w_i$ corresponds to the weight fraction of the "i th" member; and $Mz = \Sigma w_i M_i^2 / \Sigma w_i M_i = \Sigma N_i M_i^3 / \Sigma N_i M_i^2$. A wide variety of procedures is available for determining molecular weight including for example gel permeation chromatography or other chromatographic techniques, viscosity related measurements, light scattering, osmotic pressure, ultracentrifugation as well as chemical methods involving end group analysis or the like. Preferably molecular weight averages (i.e., Mn,. Mw, and Mz) and molecular weight distribution (in particular polydispersity defined as the ratio of Mw/Mn) are most conveniently measured by gel permeation chromatography as described in ASTM method D3593 and applicable references cited therein. In addition to the above conventional methods well known in the art for establishing molecular weight, an empirical method based on melt viscosity reminiscent of the Mark-Houwink inherent viscosity relationship has also been found useful for characterizing PTMEG. More specifically, the "molecular weight ratio", MWR, can be used as another measure of broadness of molecular weight distribution and is related to the melt viscosity at 40° C., $\eta_{melt}$, of the polymer as follows: $MWR = 1,160 \eta_{melt}^{.493}/Mn$ where $\eta$ is expressed in poise and Mn is determined by end group analysis by titration.

PTMEG is made commercially by polymerizing anhydrous THF in the presence of strong acid catalysts. At present most of the world's capacity is based on the use fluorosulfonic acid as the catalyst. In one commercial process when using fluorosulfonic acid as the catalyst, the polymer produced in the polymerization reactor is the sulfate ester of PTMEG which is hydrolyzed with water to obtain higher, more economic yields of the polyol product. Unreacted THF is removed from the resultant aqueous polymer dispersion by conventional steam stripping. The acidic aqueous dispersion of impure PTMEG is then subjected to washing with water. The purpose of the washing is twofold: (1) to remove the sulfuric acid and hydrofluoric acid from the polymeric dispersion and (2) to remove the low molecular weight PTMEG fraction from the polymer by taking advantage of the higher solubility of the low molecular weight species in water. Typically, the molecular weight distribution parameters of the polymer produced in the polymerization step are: polydispersity=2.0 to 2.1 and MWR=2.3 to 2.6. However, the molecular Weight distribution of commercially salable regular PTMEG should be narrower than the polymer produced in the reactor; i.e., polydispersity=1.5 to 1.8 and MWR=1.95 to 2.05. Furthermore, the acceptable ranges for molecular weight distribution parameters of narrow molecular weight PTMEG, which is desired for certain specific applications, are extremely stringent; e.g., polydispersity=1.25 to 1.40 and MWR=1.5 to 1.7.

In a conventional fluorosulfonic acid catalyzed THF polymerization system, the low molecular weight (LMW) PTMEG fraction is washed out of the polymer. Thus, commercial crude PTMEG is typically washed with water to remove low molecular weight linear oligomeric glycols. At the same time some very low molecular weight oligomeric cyclic ethers may be partially removed. This water wash step is employed also to lower the polydispersity of the product. Generally a substantial amount of aqueous acidic effluent results from the PTMEG washing. U.S. Pat. No. 4,115,408 provides a process for recovering the dissolved LMW PTMEG by converting it to tetrahydrofuran by a high temperature depolymerization process. However in any case, the water wash is Capital intensive since it results in an aqueous stream that requires distilling water off the low molecular weight fraction before discharge.

In addition to the above need for narrow molecular weight product in certain specific applications and the problems associated with water washing to in part achieve this goal, the commercial market for PTMEG has developed and/or evolved into predominant two product grades. One PTMEG of commercial interest is characterized as having a nominal number average molecular weight of 1,000 and a Mw/Mn of 1.75. The other well established product grade is characterized as having a nominal number average molecular weight of 2,000 and a Mw/Mn of 1.85. As a practical or pragmatic issue, it would be preferable for any given PTMEG plant to be able to periodically switch from the production of one grade of material to the other as the sales and market place needs dictate. However, this cannot be done by existing continuous plants because of product hold-up or residence times of the order of 20 to 24 hours in the process equipment. For example, the change from producing poly(tetramethylene ether) glycol having Mn of 1,000 to poly(tetramethylene ether) glycol having Mn of 2,000 in a commercial plant under steady state conditions results in the production during a year's time of several hundred thousand pounds of transition material with a molecular weight of 1,200 to 1,300 and extremely high polydispersity. The transition products usually cannot be blended with regular grades because of the adverse affect on performance in critical applications. Proper disposal of the unusable transition material is costly regardless of how the disposal is carried out.

The actual process for narrowing the molecular weight distribution (i.e., lowering the polydispersity and MWR) according to the instant invention begins with a PTMEG product Of broad molecular weight distribution resulting from the typical commercial manufacturing process described above using fluorosulfonic acid or the like as polymerization catalyst. The process can also be used to reduce the polydispersity and MWR of PTMEG from any other similar process including blends of different molecular weight PTMEG lots. The advantages and benefits associated with the commercial applications of membrane fractionation are viewed as being numerous and significant, particularly in view of the above mentioned commercial emphasis on flexibility to produce different grades of poly(tetramethylene ether) glycols tailored or optimized for specific polymer end-uses. For example, Mn 1,200 to Mn 1,300 transition material by use of ultrafiltration/membrane fractionation can be converted into a Mn 1,000 grade permeate suitable for use and Mn 1,600 retentate that can be blended satisfactorily with Mn 2,000 product. Alternatively, the same Mn 1,200 to 1,300 transition material can be converted to a Mn 650 grade permeate for sale and a Mn 1,700 retentate for blending with a Mn 2,000.

An alternative method of making PTMEG is by an "acetic anhydride" process. In this method, THF is polymerized with acetic anhydride in the presence of a solid acid catalyst. The polymer, separated from the catalyst, is converted to PTMEG by conventional methanolysis process. Typically PTMEG produced in this fashion has considerable content of low molecular weight oligomer (PTMEG 250). For example, the Mn 1,600 retentate from a first fractionation can by further membrane fractionation yield Mn 250 as a permeate and excellent Mn 2,000 retentate. Another variation is to make Mn 800 material in the reactor from the "acetic anhydride" process and use ultrafiltration/membrane fractionation to give a Mn 250 permeate and a retentate of Mn 1,000 grade. Thus the improved process according to the instant invention affords a degree and level of product flexibility as well as process flexibility heretofore unknown in the commercial production of PTMEG. The improved process can also be viewed as an alternative, adjunct, or at least a partial replacement for the water wash step and is also felt to be advantageously used in combination with short-path distillation as a method to achieve the above-mentioned benefits. Furthermore, PTMEG is very hygroscopic. Water in PTMEG is a source of constant concern to polyurethane manufacturers since water reacts with isocyanates in competition with the polyols thus altering the molecular weight and stoichiometry of the polyurethane. The water content of PTMEG in retentate produced by this ultrafiltration/membrane fractionation process is <20 ppm. Also, the removal of low molecular weight (i.e., oligomeric) cyclic ethers, a common commercial concern and objective, is inherently accomplished at least for the retentate fraction.

In order to more fully illustrate and exemplify the method of reducing the polydispersity according to the present invention, a series of thirty experimental fractionations were carried out using laboratory scale equipment essentially set-up as shown in the FIGURE. In this batch system as practiced in the laboratory, the relatively low molecular weight permeate/ultrafiltrate fraction was allowed to collect for a given period of time. The concentrate or more specifically the recirculating retentate corresponding to the relatively higher molecular weight PTMEG fraction was periodically diverted to storage tank 30 at the conclusion of the individual batch processing. Tank 12 was jacketed and heated by a hot oil system at the desired temperature for fractionation depending on which type of membrane material; i.e., between 35° and 150° C. The desired constant temperature was maintained and the entire system was insulated to minimize temperature variations. In each experimental run the temperature and pressure of the fractionation was monitored and the molecular weight of the resulting permeate fraction was determined by gel permeation chromatography. The results and significance of these runs are tabulated in the text and tables of the following examples.

EXAMPLES 1–9

In order to demonstrate the ability of the present method to convert a typical commercial grade of nominally 1,000 molecular weight PTMEG to a narrower molecular weight, a series of nine experimental runs involving various membrane surfaces of varying composition and permeability were tested. In each run the staring material was a PTMEG polymer manufactured by DuPont and sold under the tradename "TERATHANE" 1,000. This starting material was known to have been produced by the fluorosulfonic acid catalysis method and already involved a low molecular weight (LMW) fractionation wash and recovery as essentially described in U.S. Pat. No. 4,115,408. The molecular weight of the starting material was measured by gel permeation chromatography to be Mn=951, polydispersity=1.69 and Mz=2,282. The resulting data are presented below. As can be seen from these data, the individual runs involving two membranes characterized by ACOFs of 3,000 and 1,000 respectively did not effectuate fractionation of the 1,000 molecular weight starting material. Similarly the three runs using an anisotropic stainless steel ultrafilter system were ineffective. Also, the three thin film composite membranes did not allow the PTMEG to pass through the fractionation unit. However, the cellulose acetate membrane characterized by a %NaCl permeability of <15 produced the desired fractionation and recovery of substantially narrower molecular weight PTMEG.

|   | MEMBRANES | TEMP. (°C.) | PRESSURE (PSI) | PERMEATE CHARACTERISTICS | | |
|---|---|---|---|---|---|---|
|   |   |   |   | Mn | POLYDISPERSITY | Mz |
| 1. | 3K Alpha[a] | 64.6 | 233 | 873 | 1.67 | 2,057 |
| 2. | 1K Omega[b] | 66.4 | 266 | 856 | 1.66 | 1,994 |
| 3. | CA-990 PP[c] | 67.1 | 333 | 704 | 1.49 | 1,343 |
| 4. | Carre[d] | 66.3 | 200 | 996 | 1.80 | 2,681 |
| 5. | Carre | 63.6–70 | 100 | 868 | 1.82 | 2,534 |
| 6. | Carre | 72.3–89.3 | 400 | 848 | 1.86 | 2,528 |
| 7. | HC 50 |   |   |   | No permeate |   |
| 8. | HR 95 PP |   |   |   | No permeate |   |

-continued

| MEMBRANES | TEMP. (°C.) | PRESSURE (PSI) | PERMEATE CHARACTERISTICS | | |
|---|---|---|---|---|---|
| | | | Mn | POLYDISPERSITY | Mz |
| 9. HR 98 PP | | | No permeate | | |

(a)Lab 20, Niro Filtration, Thin film composite surface, approximate cut off value (ACOF) MW 3,000
(b)Lab 20, Niro Filtration, Thin film composite surface ACOF MW 1,000
(c)Niro Filtration, Cellulose Acetate <15% NaCl Permeability.
(d)Substrate A-2045-55-02

EXAMPLES 10–22

In order to demonstrate the ability of the present method to also act as an alternative to the above mentioned LMW fractionation wash and to demonstrate the efficacy of the method relative to fractionating the broader molecular weight distribution produced by the "acetic anhydride" (ACAN) method, a series of thirteen additional experimental runs again involving various membrane surfaces of varying composition and permeability were tested. In each run the staring material was a blend of the PTMEG polymer manufactured by DuPont and sold under the tradename "TERATHANE" 1,000 along with 6.5 weight percent of a low molecular weight oligomeric water wash extract having a nominal number average molecular weight of 250 and a low Mw/Mn added back to the PTMEG. The molecular weight of the blend was determined by gel permeation chromatography to be Mn=817, polydispersity=1.88 and Mz=2,607. The resulting data for these additional runs are presented below. As can be seen from these data, the individual runs involving two membranes characterized by ACOF's of 3,000 and 1,000 are the most effective for fractionating the starting blend.

| MEMBRANES | TEMP. (°C.) | PRESSURE (PSI) | PERMEATE CHARACTERISTICS | | |
|---|---|---|---|---|---|
| | | | Mn | POLYDISPERSITY | Mz |
| 10. 3K Alpha | 47.5 | 225 | 666 | 1.59 | 1,659 |
| 11. 1K Omega | 47.5 | 260 | 667 | 1.66 | 1,814 |
| 12. HC 50 | 47.5 | 295 | 793 | 1.76 | 2,328 |
| 13. 990 PP | 47.5 | 330 | 647 | 1.70 | 1,954 |
| 14. 3K Alpha | 65.5 | 233 | 665 | 1.57 | 1,590 |
| 15. 1K Omega | 65.5 | 266 | 683 | 1.64 | 1,809 |
| 16. HC 50 | 65.5 | 300 | 812 | 1.78 | 2,417 |
| 17. 990 PP | 65.5 | 334 | 749 | 1.81 | 2,356 |
| 18. Carre Tube | 63.9–65.6 | 100 | 887 | 1.76 | 2,553 |
| 19. Carre Tube | 66–72.7 | 200 | 834 | 1.83 | 2,556 |
| 20. Carre Tube | 74.6–84.9 | 400 | 775 | 1.90 | 2,491 |
| 21. HR 95 PP | | 400 | No permeate | | |
| 22. HR 98 PP | | 400 | No permeate | | |

EXAMPLES 23–30

In order to further demonstrate the ability of the present method to Convert typical transition product of nominally 1,300 to 1,400 molecular weight PTMEG to a narrower molecular weight fractions that can then at least be blended back into either the nominal 1,000 or 2,000 molecular weight commercial grade materials, a series of eight experimental runs were performed. In each run the starting material was a blend of equal amounts of three PTMEG polymer products having molecular weights of 1,000, 1,400 and 2,000. The molecular weight of the starting material blend was measured by gel permeation chromatography to be Mn=1,269, polydispersity=1.93 and Mz=4,021. The resulting data are presented below. As can be seen from these data, the individual runs involving membrane characterized by ACOF's of 3,000 and the anistotropic stainless steel ultrafilter system operated at 100 psig were most effective in achieving fractionation and recovery of substantially narrower molecular weight PTMEG.

| MEMBRANES | TEMP. (°C.) | PRESSURE (PSI) | PERMEATE CHARACTERISTICS | | |
|---|---|---|---|---|---|
| | | | Mn | POLYDISPERSITY | Mz |
| 23. 3K Alpha | 65.2–66.1 | 233 | 940 | 1.56 | 2,171 |
| 24. 1K Omega | 65.2–66 | 266 | 1080 | 1.73 | 2,939 |
| 25. HC 50 | 65.2–65.4 | 280 | 1224 | 1.76 | 3,327 |
| 26. HR 95 PP | 65.1–65.2 | 367 | 1222 | 1.78 | 3,363 |
| 27. HR 98 PP | 65.2–66.1 | 400 | 1175 | 1.80 | 3,290 |
| 28. Carre Tube | 73.2–74.7 | 100 | 858 | 1.79 | 2,399 |
| 29. Carre Tube | 76.5–80 | 200 | 1020 | 1.84 | 3,017 |
| 30. Carre Tube | 80–88.2 | 400 | 1129 | 1.83 | 3,250 |

Having thus described and exemplified the invention with a certain degree of particularity, it should be appreciated that the following claims are not to be so limited but are to be afforded a scope commensurate with the wording of each element of the claim and equivalents thereof.

We claim:

1. A process for fractionating poly(tetramethylene ether) glycols comprising the steps of:
    (a) providing a cross-flow membrane fractionation means characterized by a permeable or semipermeable membrane surface having a feed/retentate side and a permeate/ultrafiltrate side for separating relatively lower molecular weight poly(tetramethylene ether) glycol species from relatively higher molecular weight poly(tetramethylene ether) glycol species;

(b) passing a feed stream of molten poly(tetramethylene ether) glycols, consisting of a distribution of poly(tetramethylene ether) glycol species substantially free of solvent, across the feed/retentate side of the membrane surface of said membrane fractionation means at a temperature above the melt temperature of said-poly(tetramethylene ether) glycol and below the decomposition temperatures of the membrane surface and poly(tetramethylene ether) glycol such that at least a portion of relatively lower molecular weight poly(tetramethylene ether) glycol species pass preferentially through said permeable or semipermeable membrane surface; and (c) recovering from said membrane fractionation means a permeate/ultrafiltrate fraction rich in lower molecular weight poly(tetramethylene ether) glycol species characterized by a numerically smaller polydispersity than the original feed stream of molten poly(tetramethylene ether) glycols and a retentate fraction rich in higher molecular weight poly(tetramethylene ether) glycol species also characterized by a numerically smaller polydispersity than the original feed stream of molten poly(tetramethylene ether) glycols.

2. The process of claim 1 wherein the poly(tetramethylene ether) glycol being fed to said cross-flow membrane fractionation means has a number average molecular weight of from 400 to 4,000.

3. The process of claim 2 wherein the permeable or semipermeable membrane surface comprises polysulfones, cellulose acetate or their derivatives.

4. The process of claim 2 wherein the permeable or semipermeable membrane surface comprises sintered stainless steel coated with substrates consisting of titanium dioxide, zirconium oxide, and polyacrylic acid in a tubular membrane.

5. The process of claim 1 wherein the poly(tetramethylene ether) glycol retentate fraction recovered from said cross-flow membrane fractionation means is characterized by a water content of less than 20 ppm and substantially no oligomeric cyclic ether content.

* * * * *